United States Patent
Jiravanichkul et al.

(10) Patent No.: US 11,839,485 B2
(45) Date of Patent: Dec. 12, 2023

(54) METHOD, COMPUTING DEVICE AND WEARABLE DEVICE FOR SLEEP STAGE DETECTION

(71) Applicant: Nitto Denko Corporation, Osaka (JP)

(72) Inventors: Maneerat Jiravanichkul, Bangkok (TH); Thada Jirajaras, Bangkok (TH); Visit Thaveeprungsriporn, Singapore (SG); Pannawit Srisukh, Bangkok (TH); Pongsarun Thiamtawan, Bangkok (TH)

(73) Assignee: Nitto Denko Corporation

( * ) Notice: Subject to any disclaimer, the term of this patent is extended or adjusted under 35 U.S.C. 154(b) by 463 days.

(21) Appl. No.: 16/977,194

(22) PCT Filed: Feb. 28, 2019

(86) PCT No.: PCT/SG2019/050111
§ 371 (c)(1),
(2) Date: Sep. 1, 2020

(87) PCT Pub. No.: WO2019/168474
PCT Pub. Date: Sep. 6, 2019

(65) Prior Publication Data
US 2021/0153807 A1 May 27, 2021

(30) Foreign Application Priority Data
Mar. 2, 2018 (SG) .............. 10201801850P

(51) Int. Cl.
*A61B 5/00* (2006.01)
*G16H 40/67* (2018.01)
(Continued)

(52) U.S. Cl.
CPC ........ *A61B 5/4812* (2013.01); *A61B 5/02405* (2013.01); *A61B 5/4848* (2013.01);
(Continued)

(58) Field of Classification Search
CPC . A61B 5/4812; A61B 5/02405; A61B 5/4848; A61B 5/7221; A61B 5/7267;
(Continued)

(56) References Cited

U.S. PATENT DOCUMENTS

| | | | |
|---|---|---|---|
| 9,655,559 | B2 | 5/2017 | Chan et al. |
| 2009/0198145 | A1 | 8/2009 | Chow |

(Continued)

FOREIGN PATENT DOCUMENTS

| | | | |
|---|---|---|---|
| AU | 2015268701 A1 | 1/2016 | |
| CN | 105982643 A | 10/2016 | |

(Continued)

OTHER PUBLICATIONS

Himmetoglu, "Stacking Models for Improved Predictions", KDnuggets (Year: 2017).*

(Continued)

*Primary Examiner* — Eric F Winakur
*Assistant Examiner* — Jonathan Drew Moroneso
(74) *Attorney, Agent, or Firm* — Lerner David LLP

(57) ABSTRACT

A method of sleep stage detection using vital sign features derived from PPG signals. The method includes performing a logistic regression operation based on a machine learning classifier model to calculate an indication value for an intermediate epoch. The indication value is calculated based on the vital sign features for the intermediate epoch as well as those of the preceding and succeeding epochs. The method then detects the sleep stage of the corresponding intermediate epoch based on the indication value for the corresponding intermediate epoch.

17 Claims, 14 Drawing Sheets

(51) Int. Cl.
  *G16H 50/30* (2018.01)
  *G16H 50/20* (2018.01)
  *G16H 20/10* (2018.01)
  *A61B 5/024* (2006.01)

(52) U.S. Cl.
  CPC .......... *A61B 5/7221* (2013.01); *A61B 5/7267* (2013.01); *G16H 20/10* (2018.01); *G16H 40/67* (2018.01); *G16H 50/20* (2018.01); *G16H 50/30* (2018.01)

(58) Field of Classification Search
  CPC ....... A61B 5/4839; A61B 5/681; A61B 5/725; A61B 5/024; A61B 5/4815; G16H 20/10; G16H 40/67; G16H 50/20; G16H 50/30; G16H 20/70; G16H 50/70; G16H 50/50; G06N 3/045; G06N 3/084; G06N 20/00
  See application file for complete search history.

(56) References Cited

U.S. PATENT DOCUMENTS

| | | | |
|---|---|---|---|
| 2011/0218454 | A1 | 9/2011 | Low |
| 2014/0088373 | A1* | 3/2014 | Phillips .................... A61B 5/05 600/301 |
| 2015/0147418 | A1 | 5/2015 | Urade et al. |
| 2017/0055898 | A1 | 3/2017 | Bandyopadhyay et al. |
| 2017/0273617 | A1 | 9/2017 | Kaji |
| 2017/0274174 | A1 | 9/2017 | Purdon et al. |
| 2017/0360308 | A1 | 12/2017 | Fonseca et al. |
| 2018/0070839 | A1* | 3/2018 | Ritscher ............... A61B 5/4815 |
| 2018/0106897 | A1* | 4/2018 | Shouldice ............ A61B 5/4818 |

FOREIGN PATENT DOCUMENTS

| | | | |
|---|---|---|---|
| JP | 2017221413 A | 12/2017 | |
| WO | WO-2018070935 A1 * | 4/2018 | ............... A61B 5/04 |

OTHER PUBLICATIONS

Refaeilzadeh et al., "Cross-Validation", Springer Science+Business Media (Year: 2016).*
Extended European Search Report including Written Opinion for Application No. 19761655.0 dated Jul. 4, 2022, pp. 1-24.
Hayet, W. et al., "Sleep-wake stages classification based on heart rate variability", Biomedical Engineering and Informatics (BMEI 2012), Oct. 16, 2012, pp. 996-999. XP032395453.
Malik, J. et al: "Sleep-wake classification via quantifying heart rate variability by convolutional neural network", arxiv.org, Cornell University Library, Aug. 1, 2018, pp. 1-18, NY. XP080903875.
Radha, M. et al., "Sleep stage classification from heart-rate variability using long short-term memory neural networks," Scientific Reports, Oct. 2, 2019, pp. 1-11.
Wei, L. et al., "Feature fusion for imbalanced ECG data analysis", Biomedical Signal Processing and Control, Dec. 20, 2017, pp. 152-160, vol. 41, Elsevier, Amsterdam, NL. XP085499145.
Biswal, S et al., "Sleepnet: Automated Sleep Staging System via Deep Learning", "arxiv.org, Cornell University Library, 201 Olin Library, Cornell University, Ithaca, NY 14853", Jul. 2017, 17 pages, XP080779539.
Extended European Search Report for European Patent Application No. 19761655.0 dated Mar. 2, 2022, 18 pages.
Gao, X et al., "Modeling Binary Time Series Using Gaussian Processes With Application to Predicting Sleep States", "arxiv.org, Cornell University Library, 201 Olin Library Cornell University Ithaca NY 14853", Nov. 2017, 36 pages, XP080837343.
Takeda, T et al., "Time-dependent Sleep Stage Transition Model Based on Heart Rate Variability", "2015 37th Annual International Conference of the IEEE Engineering in Medicine and Biology Society", Aug. 2015, pp. 2343-2346, XP032810689.
International Preliminary Report on Patentability for Application No. PCT/SG2019/050111, dated Jun. 1, 2020, pp. 1-32.
International Search Report for Application No. PCT/SG2019/050111, dated May 16, 2019, pp. 1-7.
Written Opinion of the International Preliminary Examining Authority for Application No. PCT/SG2019/050111, dated Feb. 10, 2020, pp. 1-9.
Written Opinion of the International Searching Authority for Application No. PCT/SG2019/050111, dated May 16, 2019, pp. 1-9.

* cited by examiner

METHOD, COMPUTING DEVICE AND WEARABLE DEVICE FOR SLEEP STAGE DETECTION

CROSS REFERENCE TO RELATED APPLICATIONS

The present application is a national phase entry under 35 U.S.C. § 371 of International Application No. PCT/SG2019/050111, filed Feb. 28, 2019, published in English, which claims priority from Singapore Patent Application No. 10201801850P, filed Mar. 2, 2018, the disclosures of which are incorporated by reference herein.

TECHNICAL FIELD

The present disclosure relates generally to a method, a computing device and a wearable device for sleep stage detection, more particularly for detecting sleep stages including rapid eye movement (REM) and non-REM (NREM) based on machine learning.

BACKGROUND

A person's physical and mental states are known to be influenced by the quality of their sleep. A good quality sleep is essential for maintaining fitness, wellbeing and good mood. When asleep, a person typically transitions between a rapid eye movement (REM) stage and a non-REM (NREM) stage. Several studies have found that the REM stage plays an important role in mood regulation and memory consolidation. Furthermore, depressive disorders have been found to be closely linked to REM sleep dysregulations, such as increased REM sleep durations and shortened REM latencies. Thus, the sleep stages may be monitored to provide important information for sleep behaviour analysis and stress management, as well depressive disorder treatment, elderly care, and performance analysis. The quality of analysis and hence the quality of treatment are largely dictated by the collected data, both in terms of quality and quantity. To meet these requirements, monitoring devices employed are typically hardware intensive and complex.

The current gold standard for sleep study, is Polysomnography (PSG). This requires numerous sensors, including Electroencephalography (EEG), Electrooculography (EOG), Electromyography (EMG), Electrocardiography (ECG), and respiration sensors. Although PSG provides more information for sleep study, it is highly immobile and highly-priced, which makes it impractical for mass observations.

U.S. Pat. No. 9,655,559B2 discloses automated sleep staging using wearable sensors. The disclosed arrangement suffers from several drawbacks, such as poor accuracy and susceptibility to poor sensor readings.

It is desirable to provide a method, a computing device and a wearable device for sleep stage detection, which address at least one of the drawbacks of the prior art and/or to provide the public with a useful choice and/or an alternative choice.

SUMMARY

According to one aspect, there is provided a method of sleep stage detection, comprising: receiving a first vital sign feature including a plurality of first feature values corresponding to respective ones of a plurality of epochs; and performing a first logistic regression operation to calculate a first indication value for each intermediate one of the epochs based on the corresponding first feature value and those of preceding and succeeding ones of the epochs, the first indication value being descriptive of a sleep stage of the corresponding intermediate epoch.

The described embodiment is particularly advantageous. For example, by performing the first logistic regression operation with respect to each intermediate one of the epochs based on the first feature values of the preceding, intermediate and succeeding ones of the epochs, the first indication value descriptive of the sleep stage of each intermediate one of the epochs can be calculated. This is advantageous in that, not only the feature values of the preceding and intermediate epochs are used, but that of the succeeding epoch is also used, achieving an improved accuracy. In one embodiment, due to the minimal amount of data and processing required, the method requires less computing resources to be implemented, either in a hardware form, a software form, or a combination of both. Thus, the method is particularly suitable for but not limited to implementation using a wearable device.

The first vital sign feature may relate to one of a heart rate, a pulse shape variability and a convoluted high frequency power of heart rate variability. These vital sign features are found to relate to sleep stage and are therefore useful in detecting a sleep stage.

Preferably, the first logistic regression operation may include weighting and sigmoid operations. Logistic regression operations are less complex and more interpretable than non-linear models. It is known in the field of machine learning that complex models have higher risks of overfitting in comparison with simple models. Thus, by using logistic regression operations, sleep stage detection according to one embodiment is suitable to be performed on, for example, a wearable device. Relatively complex algorithms used in relation to convolutional neural networks for extracting HRV PSD, which involves three dimensions, may be performed on, for example, a server of a cloud service. The extraction of HRV PSD.

It is preferred that the method may further comprise: receiving a second vital sign feature including a plurality of second feature values corresponding to respective ones of the epochs; performing a second logistic regression operation to calculate a second indication value for each intermediate one of the epochs based on the corresponding second feature value and those of the preceding and succeeding ones of the epochs, the second indication value being descriptive of the sleep stage of the corresponding intermediate epoch; and performing a further logistic regression operation to determine the sleep stage of each intermediate one of the epochs based on the corresponding first and second indication values.

In the described embodiment, for example, by receiving multiple vital sign features and performing multiple logistic regression operations based on the respective vital sign features to calculate the respective indication values, the further logistic regression operation can be performed based on the indication values to determine the sleep stage of each intermediate epoch. By taking into account information of the multiple vital sign features, an improved result of sleep stage detection can be achieved. By taking into account multiple vital sign feature and performing a further logistic regression operation, the sleep stage can be detected with an improved accuracy.

It may be that one of the logistic regression operations have weight values different from those of another one of the logistic regression operations.

Preferably, the method may further comprise: receiving a third vital sign feature including a plurality of third feature values corresponding to respective ones of the epochs; and performing a third logistic regression operation to calculate a third indication value for each intermediate one of the epochs based on the corresponding third feature value and those of the preceding and succeeding ones of the epochs, wherein the further logistic regression operation is performed to determine the sleep stage of each intermediate one of the epochs further based on the corresponding third indication value if the corresponding third indication value is descriptive of the sleep stage of the corresponding intermediate epoch.

This arrangement is advantageous because the third indication value may not be indicative of the sleep stage due to, for example, uncompensated corresponding feature values of the third vital sign feature. Such a third indication value, if used in the further logistic regression operation, may impact the accuracy of sleep stage determination. Thus, by only using the third indication value only if it is descriptive of the sleep stage, an accurate result of sleep stage detection can be achieved.

According to another aspect, there is provided a method of creating a model for logistic regression, comprising: receiving a vital sign feature in association with reference sleep stage information; generating, from the vital sign feature and the reference sleep stage information, a cross validation set including a plurality of subsamples; calculate each one of the subsamples with reference to other ones of the subsamples using a model with each of a plurality of machine learning parameter sets; and associating the model with one of the parameter sets based on a comparison of the reference sleep stage information with a result of the calculation.

In one embodiment, through the use of machine learning techniques, correlation between the vital sign features and the reference sleep stage information can be ascertained efficiently to determine a parameter set for use with a model. For example, the parameter set can include a first parameter set retrieved in a first sleep period, a second parameter set retrieved in a second sleep period, and both the first and second sleep periods can be retrieved and/or stored, to be programmed into a separate model. That is to say, the parameter set for one sleep period can be different from that for another sleep period. In another example, for trending the user sleep pattern, a first parameter set is retrieved in a first sleep period, a second parameter set is retrieved in a second sleep period, and both the first and second sleep periods can be retrieved and/or stored, to be programmed in a trend model. A third parameter set is retrieved in a third sleep period, where the third sleep period is distinct and separate, through time space, from the first and second sleep periods. The third sleep period can be retrieved and/or stored, to be programmed into the trend model.

The vital sign feature may relate to one of a heart rate, a pulse shape variability and a convoluted high frequency power of heart rate variability. These vital sign features are found to relate to sleep stage and are therefore useful in detecting a sleep stage. In another embodiment, the vital sign feature may also relate to a summation of power in high frequency of heart rate variability, a summation of power in low frequency of heart rate variability, LF/HF ratio of the heart rate variability, standard deviation of heart rate. These vital sign features may be retrieved from present and/or past data from another device and are therefore useful in detecting a sleep stage.

Preferably, the method further comprises: receiving another vital sign feature in association with the reference sleep stage information, wherein the cross validation set is further generated from the another vital sign feature. By taking into account another vital sign feature, the cross validation set includes more information that can be used to accurately detect sleep stage.

The vital sign feature may be sliced by at least three consecutive epochs. The at least three consecutive epochs may include, with respect to an intermediate one of the epochs, a preceding one, the intermediate one and a succeeding one of the epochs. By taking into account the succeeding epoch, sleep stage can be detected with an improved accuracy. In a described embodiment, the at least three consecutive epochs include 11 epochs. In addition, the at least three consecutive epochs are configured to correspond to a total window period of at least 30 minutes. Sleep data can be more than one hour (e.g. 7-8 hours) in duration. By "slicing" the sleep data, in one embodiment, into hourly periods or intervals, the data resemble a sleep cycle, which allows sleep stage calculation to be performed efficiently.

The vital sign feature may be normalised. Further, the vital sign feature may be compensated for a missing portion. For example, the missing portion can be compensated for using max pooling. Such a technique is useful for reducing adverse influence of such missing portions on the detection result, which may otherwise lead to false positive or negative detection. Alternatively, such missing portions may be replaced with random values, average values, nearest values, linear interpolation, etc., depending on implementation.

According to another aspect, there is provided a method of extracting a heart rate variability feature, comprising: convolving a high frequency portion of a heart rate variability power spectral density with a convolution filter to generate a plurality of convolution values representing respective patterns of heart rate variability, the convolution filter relating to a convolutional neural network model; and selecting one of the convolution values based on a result of an activation function operation performed on the convolution values.

In one disclosed embodiment, the method is advantageous in that the correlation between the high frequency portion of the heart rate variability power spectral density and rapid eye movement (REM) is taken into consideration, where the detection of a lower power in the high frequency portion strongly indicates REM.

It is preferable that the selected convolution value corresponds to a largest value resulting from the performed activation function. The largest value corresponds to REM and/or NREM sleep stage that advantageously provides a concerted approach to deriving the sleep stage Moreover, the high frequency portion preferably ranges from 0.15 Hz to 0.4 Hz. The heart rate variability power spectral density is found to have a particularly high degree of relation with sleep stage in this frequency portion. By taking into account spectral information in this frequency range, the resultant heart rate variability feature is more indicative of the sleep stage.

The power spectral density may be normalised across the high frequency portion and a low frequency portion thereof. The normalisation rejects scales of the data but instead provides a consistent power spectral density for adaptation Preferably, the activation function operation relates to one of a rectified linear unit, a soft relu and a sigmoid function.

According to another aspect of the present disclosure, there is disclosed a method of creating a model for extracting a heart rate variability feature, comprising: receiving, in association with reference sleep stage information, a vital sign feature representing a heart rate variability power spectral density; and creating a model including a convolution filter using machine learning based on the vital sign feature with reference to the reference sleep stage information. By deriving the physiological signal using such a model, the high frequency component of heart rate variability serves as a relatively consistent basis for sleep stage detection.

The vital sign feature is preferably derived from a physiological signal for an interval of three minutes within each interval of five minutes. Power consumption can be reduced without significantly impacting the accuracy of sleep stage detection. Alternatively, the vital sign feature may be derived from the physiological signal with respect to an epoch for an interval shorter than that of the epoch.

Preferably, the vital sign feature is normalised.

The machine learning preferably includes a convolutional neural network. Convolutional neural network, CNN, algorithms for training models can relate information in both HRV PSD and sleep stage. HRV PSD can be viewed as an image that can contain a pattern of HRV changes in frequency domain over a time period. Pattern of alternating low and high power in HRV PSD that is coherent with REM and NREM sleep stage patterns can be observed in experimental data. CNN algorithms can be used to extract information of such an image.

In one disclosed embodiment, one advantage of using CNN algorithms is that CNN algorithms can process HRV PSD into a calculated value that relates to REM/NREM sleep stage by optimizing the convolution filter, activation function, data pooling method, and neural network weights that can provide a minimal or reduced prediction error. In other words, CNN algorithms can summarize or otherwise process HRV PSD into a calculated value indicative of a sleep stage through model training. The present disclosure in one example arrangement advantageously processes at least three dimensional data that includes the frequency of HRV, time domain and Power density.

It is possible to use information gathered or retrieved to be eventually applied with other information obtained from another device together with the information gathered from the wearable device. Vice versa, retrieve information such as any of the HR, HRV, and pulse shape variability, from any type of sensors, the machine learning algorithm can further refine the information.

According to another aspect, there is disclosed a method of deriving medical dosage comprising: receiving sleep stage information of a first time period; receiving and comparing sleep stage information between the first time period and a second time period; providing the reference sleep stage information causing for prescriptive medical dose.

According to another aspect, there is disclosed a method of assessing a responsiveness to a medical dosage comprising: receiving sleep stage information of a first time period; receiving sleep stage information of a second time period for comparison with that of the first time period; and assessing a responsiveness to a medical dosage occurring between the first and second time periods based on a result of the comparison.

The prescriptive medical dosage may relate to at least one of anticonvulsant, benzodiazepines and emazepam.

According to another aspect of the present disclosure, there is disclosed a computer-readable medium comprising instructions for causing a processor to perform any one of the above methods.

Preferably, the instructions are adapted to be implemented in firmware. Due to their simplicity, at least some of the above methods are particularly suitable for, but not limited to, implementation in the form of instructions in firmware.

According to another aspect of the present disclosure, there is disclosed a computing device comprising: a processor; and a storage device comprising instructions for causing the processor to perform any of the above methods.

The storage device is preferably a firmware chip. As alluded to above, at least some of the above methods may be implemented using firmware due to their simplicity and low hardware requirements.

According to another aspect of the present disclosure, there is disclosed a wearable device comprising: a storage device comprising instructions for causing the processor to perform any of the above methods.

The storage device is preferably a firmware chip. As discussed above, at least some of the above methods may be implemented using firmware.

It is preferred that the wearable device is in the form of a wristwatch, which may facilitate long term data collection.

It is envisaged that features relating to one aspect may be applicable to the other aspects.

BRIEF DESCRIPTION OF THE DRAWINGS

Example embodiments will now be described with reference to the accompanying drawings, among which.

DESCRIPTION

Figure 1:
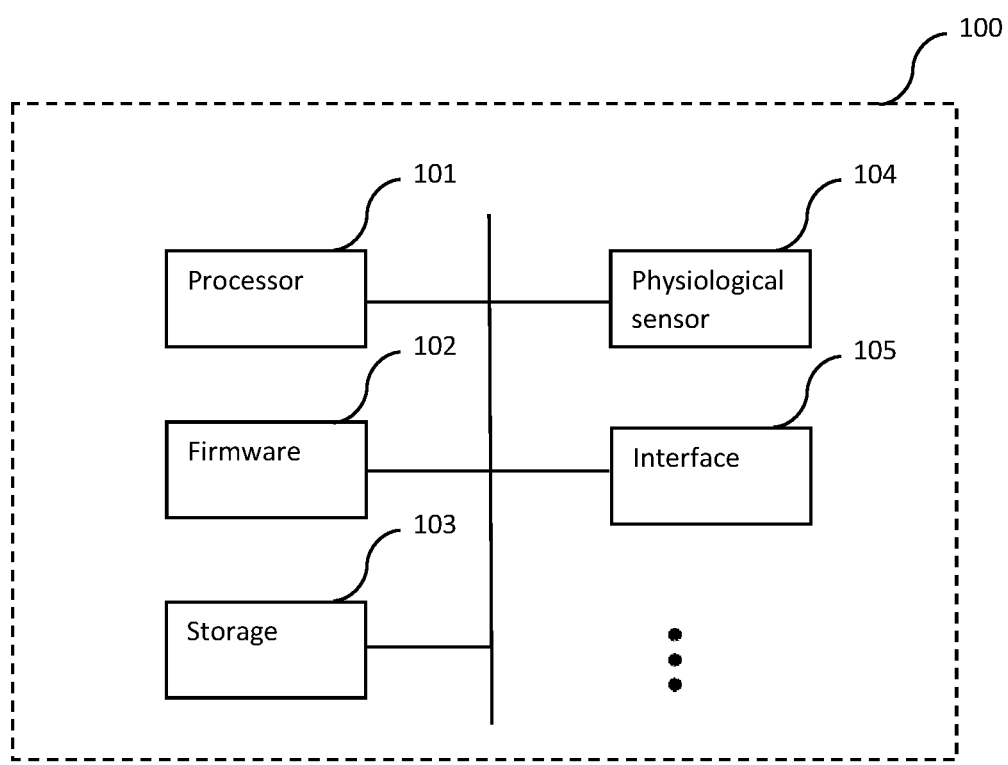
FIG. 1 illustrates an example system block diagram of a computing device according to one embodiment of the present disclosure.

FIG. 1 shows a system block diagram of an exemplary computing device 100 suitable for performing embodiments of some methods of the present disclosure. The computing device 100 includes a processor 101, a firmware chip 102, a storage device 103, a physiological sensor 104 (e.g., an electrocardiogram sensor, a photoplethysmogram sensor or a combination thereof) and a communication interface 105 (wired or wireless) operatively associated with the processor 101. It is worth noting that any type of sensor capable of physiological measurement can be used. In one embodiment, the computing device 100 takes on the form of a miniature device (e.g., a wearable device). In another embodiment, the computing device 100 takes on the form of a computer (e.g., a server). In yet another embodiment, the computing device 100 takes on the form of a mobile device. Instructions executable by the processor 101 may be stored in the firmware chip 102, the storage device 103 or a combination thereof.

Figure 2:
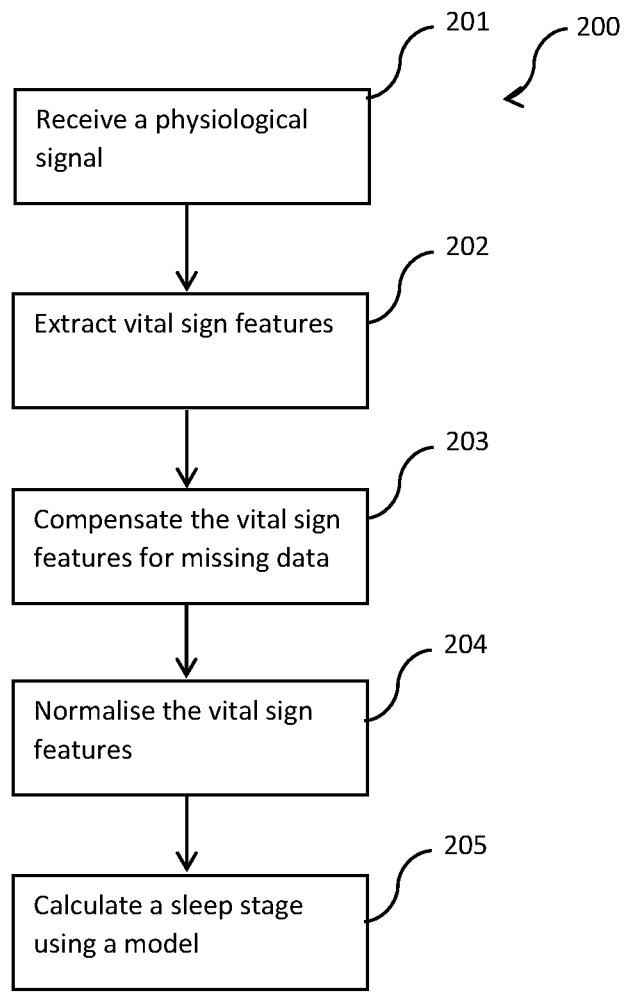
FIG. 2 shows a flowchart of a method of sleep stage detection performed by the computing device of FIG. 1.

FIG. 2 shows a flowchart of a method 200 of sleep stage detection according to one embodiment of the present disclosure. Storage and execution of instructions embodying the method 200 are as described hereinabove. Further, the computing device 100 in this embodiment takes the form of a wearable sleep stage tracking device 100. In step 201, the processor 101 receives a physiological signal from the sensor 104 worn on any suitable body part (e.g., the wrist, the upper arm, the index finger, the neck or the head).

In step 202, the processor 101 extracts, from the physiological signal, vital sign features representing a heart rate (HR), a convoluted high frequency power of heart rate variability (Conv_HF), and a pulse shape variability (PSV). In other embodiments, the vital sign features may represent additional physiological features. The vital sign feature may embody the exemplary form of a series of feature values each corresponding to a sleep stage of a corresponding epoch. In other words, each vital sign feature includes a plurality of feature values corresponding to a plurality of epochs, respectively. Take the convoluted high frequency power of heart rate variability for example, each feature value in the vital sign feature may represent a unique pattern of variability within the respective epoch. In other embodiments, however, the processor 101 may extract any number (e.g., 1, 2 or 4) of vital sign features from physiological signal.

Pulse Shape Variability (PSV) can be referred to as a standard deviation of the vital sign feature derived from a pulse shape of the input physiological signal (e.g., a PPG signal), which may be calculated based on time interval information, skewness, magnitude, integral and differential information, a frequency component, or their derivatives of a pulse for example.

Figure 6:
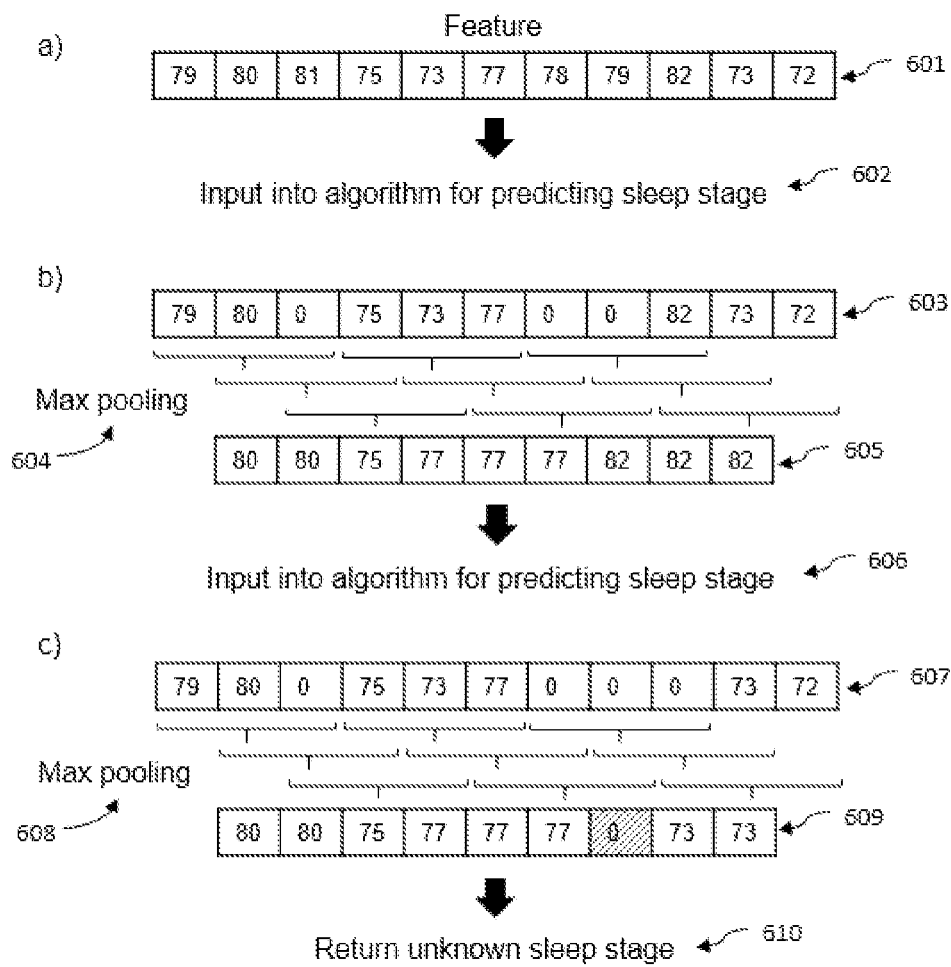
FIGS. 6(a) to 6(c) illustrate different scenarios of data error compensation performed by the computing device of FIG. 1.

In step 203, the processor 101 compensate for missing data portions in the vital sign features, if any. Missing data portions may arise from, for example, poor sensor signal quality. Through such compensation, susceptibility of a detection result to missing data portions can be reduced. Compensation for missing data portion in the vital sign features is described in detail hereinafter in relation to FIG. 6. The compensation for missing data portion may have an extraction of at least two series of inputs. Alternatively, the compensation for missing data portion may have an extraction of a set of alternate series of inputs. While another alternative may have a combination of the extraction of the at least two series of inputs and the set of alternate series of inputs.

In step 204, the processor 101 normalise the vital sign features, whether compensated or not.

In step 205, the processor 101 calculates (e.g., determines, detects or classifies) a sleep stage for each epoch from the processed vital sign features using at least one model (e.g., learned model). In this step, the processor 101 performs the function of a machine learning classifier, calculating a sleep stage for each epoch from the vital sign features. The sleep stage is determined to be one of rapid eye movement (REM) and non-REM (NREM) based a result of the calculation. This step of calculation is described in further detail hereinafter in relation to FIGS. 7, 8 and 9. The at least one model may be stored on the firmware chip 102 or the storage device 103. However, the at least one model may be created, developed or trained using machine learning on any computing platform, which is described in detail hereinafter. Where the at least one model is separately stored on a cloud server, retrieval of the at least one model by the processor 101 is, in one arrangement, based on the processor 101 communicating through the communication interface 105 connecting or linking to the cloud server. The vital sign features may, in an alternative embodiment, be provided by the processor 101 to a cloud server running the at least one model for sleep stage calculation. Thereafter, the processor 101 of the computing device 100 may request (e.g., retrieve from) the cloud server for the calculated result of sleep stage. In one embodiment, the calculated result of sleep stage can be transferred to another device programmed to combine or extract the calculated result of sleep stage with information in the other device for calculation. In other words, the calculation of sleep stage can be partially or wholly offloaded by the processor 101 to an associated processing platform such as the cloud server. The calculated or detected sleep stage of each epoch may be processed, by the processor 101 or otherwise, into a sleep stage hypnogram.

For the purpose of step 205, a model is used for machine learning classification (e.g., logistic regression). Creating (e.g., training) of the model is described below in relation to FIG. 3A. Once the new model is trained (i.e., a parameter set is associated with the model), the associated parameter set, which may include a set of constant numbers, may be stored on the firmware chip 102 of the computing device 100. Model training/re-training or adaptive modelling may be performed in real-time and the parameter set, if not stored on the firmware chip, may need to be externally retrieved from, for example an associated server device on which the parameter set is stored. The parameter set can be transferred to a server hosting a cloud service so as to enable future, long-term tracing, trending and tracking of user sleep patterns. In contrast, existing PSG techniques cannot be used to check user sleep patterns in such an efficient manner due to their immobile nature.

Therefore, it can be understood that the machine learning algorithms are used for sleep stage detection based on the vital sign features. The machine learning algorithms may be implemented using available machine learning tools. The logistic regression may be implemented using, for example, the MATLAB programming language. The machine learning algorithm (e.g., logistic regression) searches for the linear boundary, which is the linear combination of the input features, that can best separate the input features into two classes. This can be done by reducing errors of the system in classifying the training data. The resultant output is a set of linear combination of the features diverted to being represented by said one of the parameter sets. This is considered as a model. This model can be applied with a new set of inputs to detect a class of interest, which is REM or NREM sleep stage in the scenario of FIG. 2. Machine learning may also be used to derive vital sign features, which is described below.

Figure 3A:
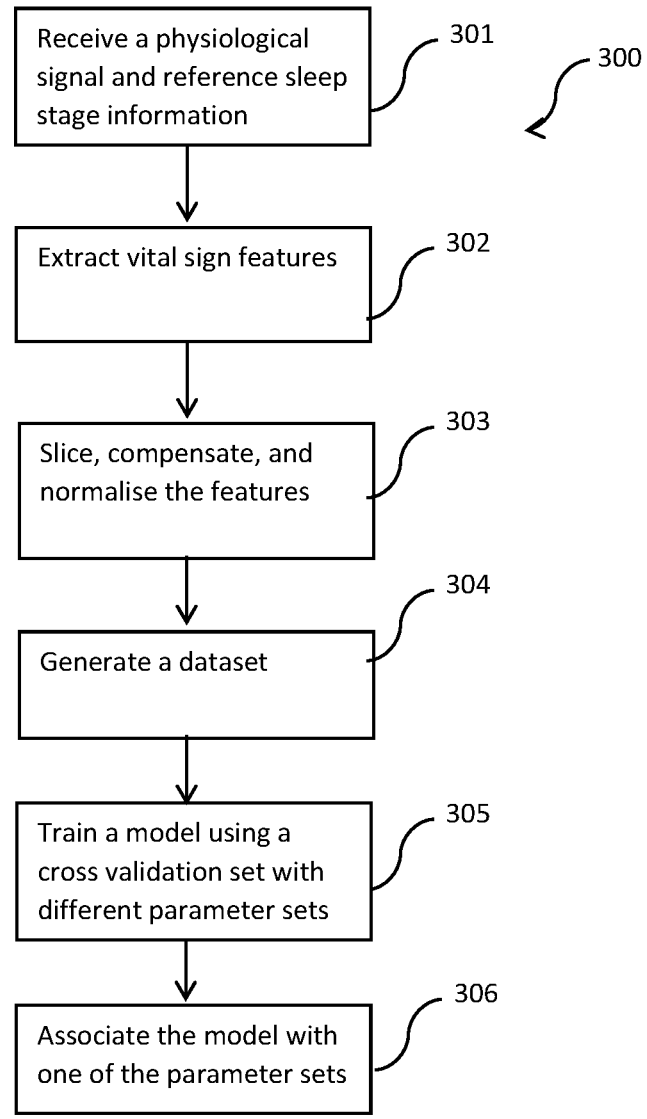
FIG. 3A shows a flowchart of a method for creating a model for logistic regression performed by the computing device of FIG. 1.

FIG. 3A shows a flowchart of a method 300 of creating a model for logistic regression, according to one embodiment of the present disclosure. The computing device 100 in this embodiment takes the form of a server device 100 configured to perform machine learning operations. The created model may be used for the purpose of step 205.

In step 301, the processor 101 receives, in association with reference sleep stage information, a physiological signal via the communication interface 105. The physiological signal may otherwise be received from the physiological sensor 104 in association with the reference sleep stage information. The reference sleep stage information and the physiological signal may be received simultaneously or otherwise. The reference sleep stage information is provided by a reference device, which may be one tested and approved by an authority. The reference sleep stage information can be derived from, for example, a medical device approved by the FDA to provide around 89% agreement of sleep stage detection to the gold standard.

In step 302, the processor 101 in this embodiment extracts, from the physiological signal, vital sign features representing a heart rate (HR), a convoluted high frequency power of heart rate variability (Conv_HF), and a pulse shape variability (PSV), respectively. In other embodiments, the vital sign features may represent additional physiological features of other types.

In step 303, the processor 101 processes the vital sign features by, in any suitable order, slicing at least three consecutive epochs that, in this embodiment, have a total span of window period of at least one hour, compensating for any missing data portions and normalising the slices by the standard score of the slices. Alternatively, the total span of window period may be at least 30 minutes. In another embodiment, a mixture of different total spans of window period may be adopted. For example, there may be at least four window periods of one hour and at least six window periods of 30 minutes, resulting in a total span of at least seven hours. For a total span of at least eight hours, the mixture may be, for example, at least five window periods of one hour and at least six window periods of 30 minutes.

In step 304, the processor 101 combines the processed vital sign features with the reference sleep stage information to generate a dataset consisting of a plurality of subsamples. A cross validation set for model training and a blind test set for model evaluation can be derived from the dataset. The cross validation set includes, or is partitioned into, (k) equal-sized subsamples.

In step 305, the processor 101 calculates (e.g., determines, predicts or estimates) each one (1) of the subsamples in the cross validation set with reference to other ones (k−1) of the subsamples in the cross validation set using a model with each of a plurality of machine learning parameter sets. In other words, each one (1) of the subsamples is calculated by the processor 101 using other ones (k−1) of the subsamples. This calculation process is repeated (k) times for each machine learning parameter set so that each subsample in the cross validation set serves as a calculation target for calculation by the processor 101 using the other subsamples in the cross validation set. Thus, said one of the subsample may be referred to as a target subsample unknown to the model while the other ones of the subsamples may be referred to as training subsamples serving as a basis for calculating the target subsample. With such an arrangement, each subsample serves once as a target subsample without "contaminating" the training subsamples. The calculated sleep stage information therefore represents a generalised performance rather than an overfitting performance.

Following the calculation, the processor 101 combines, for each parameter set, the calculated target subsamples to form calculated sleep stage information for comparison with the reference sleep stage information.

In step 306, the processor 101 associate the model with one of the parameter sets based on a comparison of the calculated sleep stage information with the reference sleep stage information. In particular, the parameter set which yields the calculated sleep stage information that most closely resembles the reference sleep stage information is associated with the model for achieving the highest calculation accuracy (or the lowest calculation error).

Figure 3B:
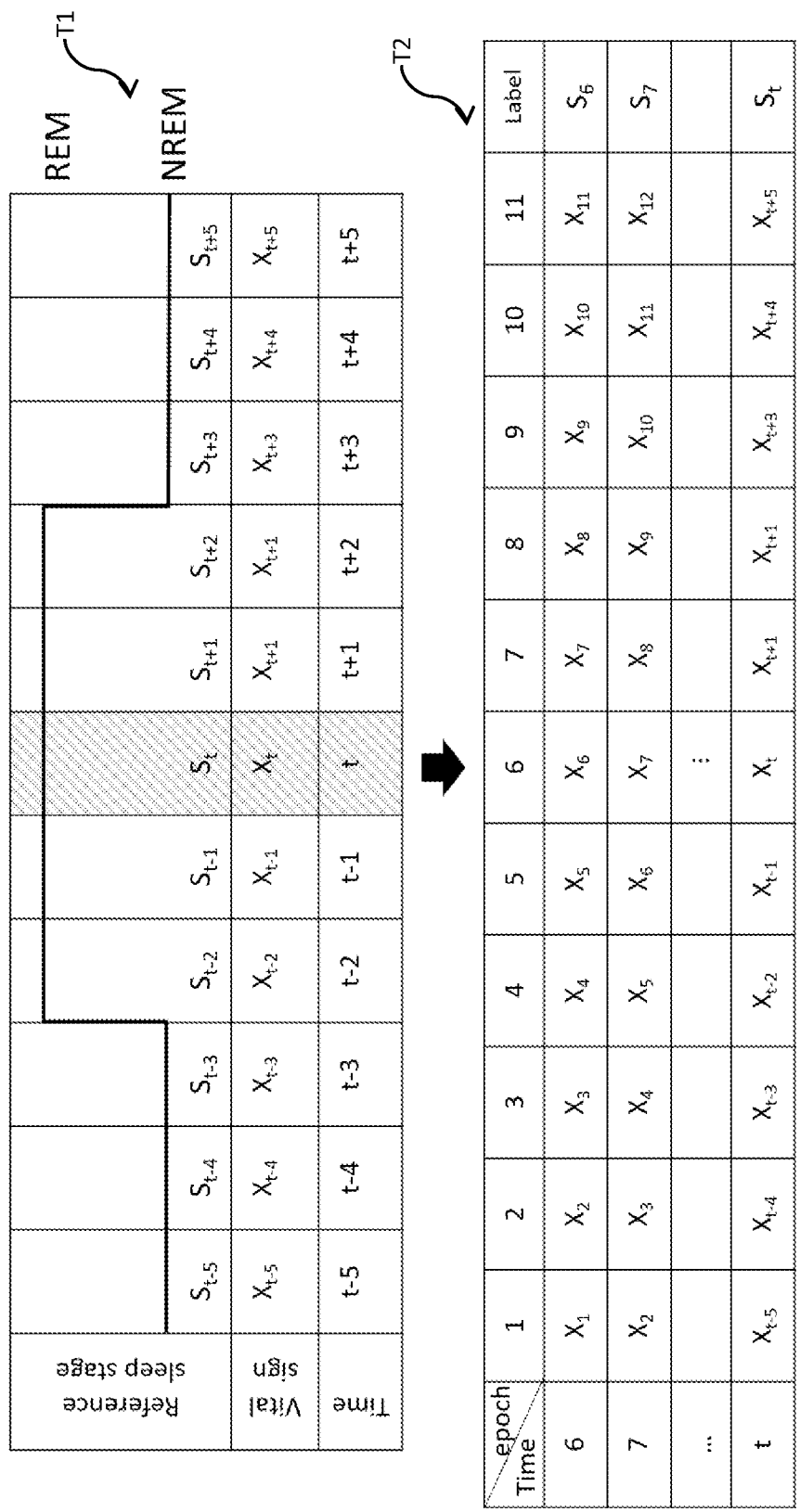
FIG. 3B shows an example of generation of training dataset.

FIG. 3B shows an example of generation of training dataset, showing two tables labelled T1 and T2, respectively. In this example, referring to table T1, a training dataset for training a logistic regression model of a vital sign feature is created by extracting the feature values at time t−5 to t−1 (preceding epochs), t, (intermediate epoch), and t+1 to t+5 (succeeding epochs), which together represent 11 feature values ($X_{t-5}$ to $X_{t+5}$) of the vital sign feature. In another example, a training dataset for training a logistic regression model of a vital sign feature is created by extracting the feature values at time t−2 to t−1 (preceding epochs), t, (intermediate epoch), and t+1 to t+2 (succeeding epochs), which together represent 5 feature values ($X_{t-2}$ to $X_{t+2}$) of the vital sign feature. The corresponding reference sleep stage at the epoch of t is marked by cell (St). The algorithm then rearranges the 11 feature values ($X_{t-5}$ to $X_{t+5}$) and the corresponding reference sleep stage (St), then the algorithm treats the rearranged feature values and the corresponding reference sleep stage as a training data set. The training data set is shown in Table T2. For each intermediate epoch at the respective time t, the corresponding reference sleep stage is appended to the corresponding 11 feature values ($X_{t-5}$ to $X_{t+5}$). A linear relationship between the feature values ($X_{t-5}$ to $X_{t+5}$) at the 11 consecutive epochs and indicative of the corresponding reference sleep stage (St) of REM or NREM can be calculated. The linear relationship defines weights and can be used to calculate an indication value at a particular epoch corresponding to one of REM and NREM with low error. In another embodiment, the time taken to extract the feature values of each vital sign feature may be extended to be longer.

Figure 4:
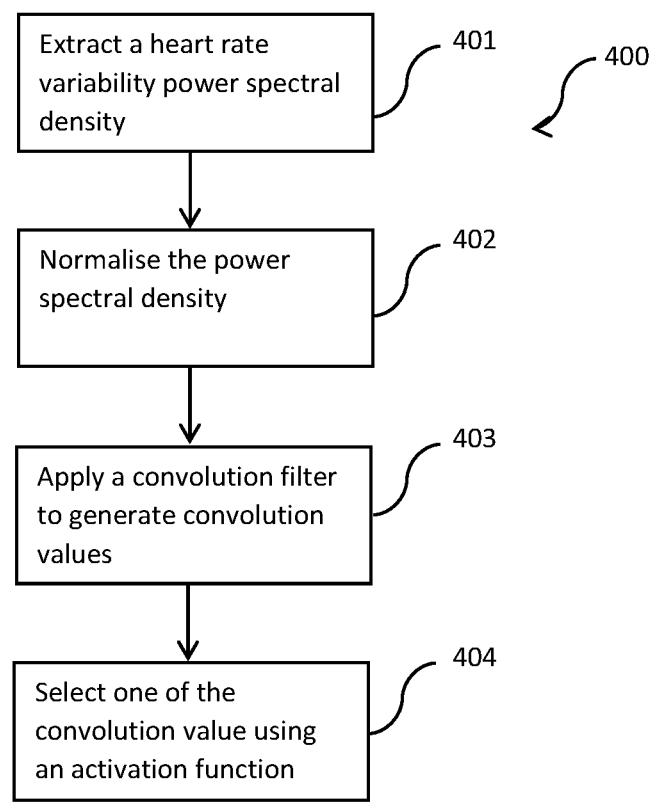
FIG. 4 shows a flowchart of a method for extracting a heart rate variability feature performed by the computing device of FIG. 1.

FIG. 4 shows a flowchart of a method 400 of extracting a heart rate variability feature, which can be performed independently or as part of step 202 of the method 200. The computing device 100 in this embodiment takes the form of a wearable sleep stage tracking device 100.

In step 401, the processor 101 extracts, from a physiological signal received by the computing device 100, a heart rate variability power spectral density based on pulse interval detection.

In step 402, the processor 101 normalises the power spectral density by dividing power at each frequency by a total power across low and high frequency portions of the spectrum, where the low frequency portion ranges from 0.04 Hz to 0.15 Hz and the high frequency portion ranges from 0.15 Hz to 0.4 Hz.

In step 403, the processor 101 convolves the high frequency portion of the power spectral density with a convolution filter to generate a plurality of convolution values representing respective heart rate variability features. Each convolution value represents a pattern of high and low powers in the high frequency portion of the heart rate variability power spectral density. The convolution filter relates to a convolutional neural network model, which will be described hereinafter.

In step 404, the processor 101 performs an activation function on the convolution values and selects one of the convolution values based on a result of the activation function. In particular, the result of the activation function indicates a resemblance relationship between the pattern of each convolution value with the actual sleep stage. The selected convolution value serves as a vital sign feature representing a convoluted high frequency power of heart rate variability (Conv_HF).

Figure 5:
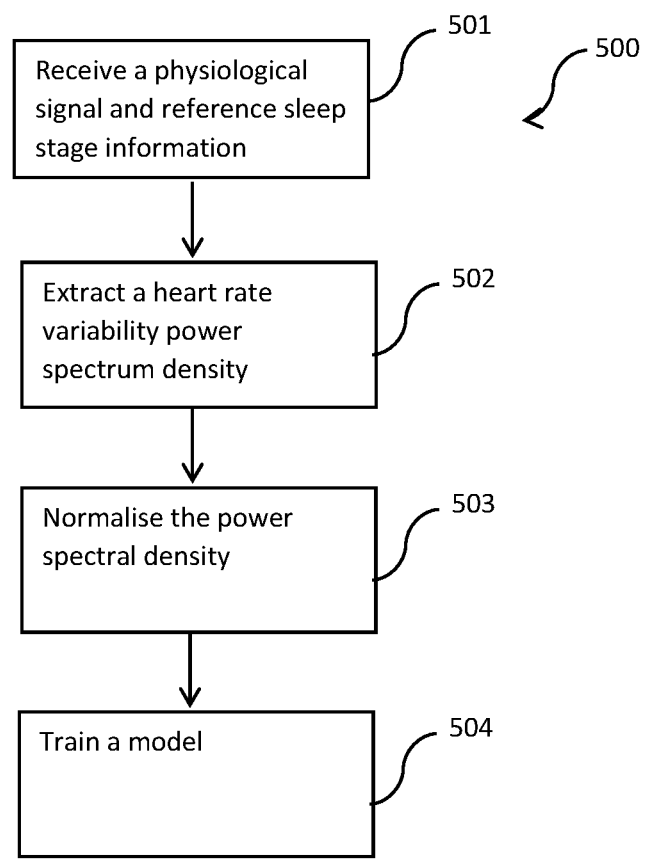
FIG. 5 shows a flowchart of a method for creating a model for extracting a heart rate variability feature performed by the computing device of FIG. 1.

FIG. 5 shows a flowchart of a method 500 of creating a model for extracting a heart rate variability feature, according to one embodiment of the present disclosure. The computing device 100 in this embodiment takes the form of a desktop personal computer 100 with sufficient processing resources for machine learning operations.

In step 501, the processor 101 receives, in association with reference sleep stage information, a physiological signal via the communication interface 105. The physiological signal may otherwise be received from the physiological sensor 104 in association with the reference sleep stage information. The reference sleep stage information and the physiological signal may be received simultaneously or otherwise. The reference sleep stage information is provided by a reference device, which may be one tested and approved by authority. Alternatively, the reference sleep stage information may be provided by a wearable device tested and approved by an authority.

In step 502, the processor 101 extracts, from each interval of the physiological signal of at least three minutes (e.g., five minutes), a vital sign feature representing a heart rate variability power spectrum density. The reason for dividing the signal into intervals of at least three minutes is that this step is for dividing a signal into several epochs and for extracting features in each epoch. In other words, extraction of the vital sign feature from the physiological signal is performed for each of a plurality of intervals into which the physiological signal is divided, with each interval being at least three minutes in duration. Without performing this step, the extracted HRV feature will represent the signal of, for example, the whole sleep session instead of specific time periods or epochs during the session. In this embodiment, each interval is five minutes and, within each interval, only three minutes of the corresponding portion of the physiological signal are used for deriving or extracting the vital sign features. In other words, the vital sign feature is derived from the physiological signal for three minutes within each interval of five minutes. This means that within each interval of five minutes, the relevant components for feature extraction operate only for three minutes, thereby reducing power consumption. In other embodiments, each interval may be other than five minutes, and within the interval, the corresponding portion of the physiological signal used for feature extraction may be other than three minutes in duration.

In step 503, the processor 101 normalises the power spectral density by dividing power at each frequency by a total power across low and high frequency portions of the spectrum, where the low frequency portion ranges from 0.04 Hz to 0.15 Hz and where the high frequency portion ranges from 0.15 Hz to 0.4 Hz.

In step 504, the normalized HRV PSD and reference's sleep stages of the training data set are inputted into machine learning algorithm, particularly convolutional neural network. The model, which comprises convolution filter, activation function, and data pooling, with acceptable or highest accuracy is selected and used for extracting Conv_HF feature, for example, in the method 400.

In particular, the model can be trained with the convolutional neural network, CNN, and algorithm using existing toolboxes, such as "mxnet" based on the programming language "R". Firstly, a training set comprising HRV PSD (feature) and the associated REM/NREM sleep stages (label) are input into the CNN algorithm. The CNN algorithm performs training by calculating the best convolution filter and neural network weights that yield the lowest classification or detection error. The training process begins with a random initialization of the model filter and weights. Next, backpropagation process is performed to calculate a gradient toward to a lower error and to adjust weights in every iteration. To obtain the model that gives a reduced or minimal error without overfitting, the model is fine-tuned by determining the appropriate model parameters (e.g. size of convolution filter, type of activation function, data pooling method, number of hidden layers, training iteration) that give the lowest error in the validation set. In such a manner, the optimized model that comprises convolution filter, activation function, and data pooling method is selected and is used to derive HRV PSD into Conv_HF feature.

As discussed hereinabove in relation to steps 203 and 303, data error (e.g., missing data portions) may occur. Where the processor 101 detects such an error in a vital sign feature, the processor 101 in this embodiment attempts to compensate for the data error. If the data error is thus rectified, the compensated vital sign feature is used in the subsequent steps for sleep stage detection. However, if the data error persists, the epoch is identified to be "unknown" in order to preserve the reliability of sleep stage detection. FIGS. 6(a) to 6(c) illustrate respective scenarios of data error compensation by the processor 101 with respect to a vital sign feature. The vital sign feature is exemplified to take the form of a sequence of feature values each corresponding to a respective epoch.

In FIG. 6(a), the processor 101 detects no missing feature value in the vital sign feature 601. No compensation is performed and the feature values of the vital sign feature are used in the subsequent step (e.g., algorithm operations) 602. In FIG. 6(b), the processor 101 detects three missing feature values of zero in the vital sign feature 603, two of which are consecutive. The processor 101 compensate for the missing feature values by, for each intermediate feature value with a preceding feature value and a succeeding feature value, selecting the largest one of the three feature values to form a new series of feature values of a compensated vital sign feature 605. Such a technique may be referred to as "max pooling" 604. The compensated vital sign feature 605 is in turn used in the subsequent step 606 (e.g., algorithm operations). In FIG. 6(c), the processor 101 detects four missing feature values of zero, three of which are consecutive, in the vital sign feature 607. The processor 101 compensate for the missing feature values in a similar manner using max pooling 608, resulting in a compensated vital sign feature 609. In this scenario, the three consecutive missing feature values, after compensation, result in another feature value of zero in the compensated vital sign feature 609. Since the data error persists, the processor 101 returns an unknown sleep stage (represented by a feature value of "0" in this case) for the epoch with the persistent error (the shaded block) in step 610 to preserve the reliability of sleep stage detection. It should be noted that other forms of data error correction or compensation are applicable.

Figure 7:
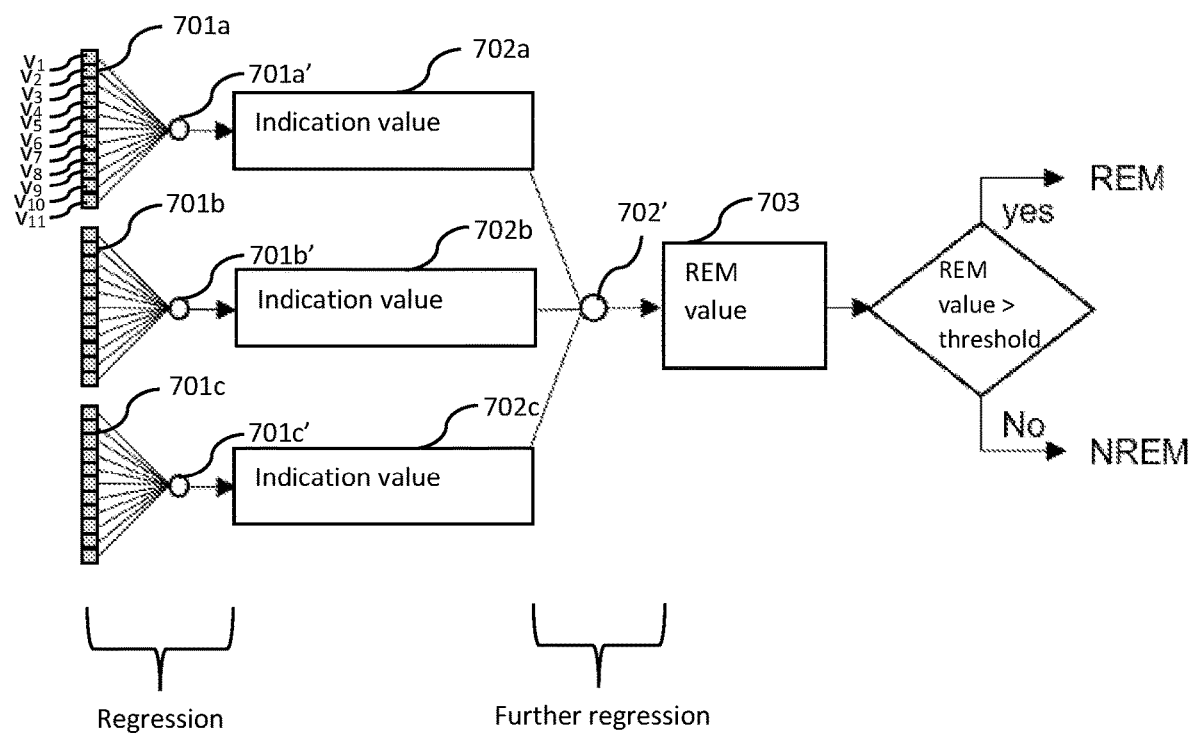
FIG. 7 shows an example scenario of sleep stage calculation involving a plurality of logistic regression operations followed by a further logistic regression operation and three vital sign features, performed by the computing device of FIG. 1.

Step 205 of the method 200 as discussed above involves calculating a sleep stage for each epoch using a model. Shown in FIG. 7 is an example scenario where the processor 101 calculates in step 205 a sleep stage for each intermediate epoch from three vital sign features 701a-701c (e.g., a heart rate, a pulse shape variability and a convoluted high frequency power of heart rate variability, respectively), with each vital sign feature 701a-701c representable by a respective series of feature values $v_1$-$v_{11}$ (only 11 shown for each vital sign feature 701a-701c in FIG. 7). For each vital sign feature 701a-701c, the processor 101 performs a respective logistic regression operation 701a'-701c' to calculate an indication value 702a-702c for each intermediate epoch (i.e., each intermediate one of the epochs) based on the corresponding feature value $v_6$ and those $v_1$-$v_6$, $v_7$-$v_{11}$ of neighbouring epochs. The neighbouring epochs are epochs temporally neighbouring the respective intermediate epoch. In this case, the neighbouring epochs includes five preceding epochs (corresponding to the respective feature values $v_1$-$v_5$), which are five epochs immediately preceding the intermediate epoch (corresponding to the feature value $v_6$), and five succeeding epochs (corresponding to the respective feature values $v_7$-$v_{11}$), which are five epochs immediately succeeding the intermediate epoch. However, in other embodiments, the neighbouring epochs may include any numbers (e.g., 1, 2 or 3) of preceding and succeeding epochs. Each indication value 702a-702c is descriptive or indicative of the sleep stage of the respective intermediate epoch.

In this embodiment, each logistic regression operation 701a'-701c' is performed by the processor 101 using (or with reference to) a respective model representing weight and sigmoid functions. That is to say, for each of the vital sign features 701a-701c, the processor 101 performs the respective logistic regression operation 701a'-701c' to calculate the indication value 702a-702c for each intermediate one of the epochs based on the corresponding feature value $v_6$ and those $v_1$-$v_5$, $v_7$-$v_{11}$ of the neighbouring ones of the epochs. The indication value 702a-702c thus calculated is descriptive or indicative of the sleep stage of the corresponding intermediate epoch. More particularly, for each model, the model includes a plurality of weights and a sigmoid function. The number of the weights corresponds to the total number of the preceding, intermediate and succeeding epochs, which, in this embodiment, is 11. In this embodiment, the models use the same sigmoid functions with respective sets of weights. The set of weights for one model may be different from those for another model. The terms "weight" and "weights" as used herein means "weight value" and "weight values", respectively. As alluded to above, the weights of each vital sign feature represent a relationship (a linear combination) of the feature values of the vital sign feature that best or ideally represent or describe the sleep stage of a particular epoch. Thus, each such linear combination of one vital sign feature may be same or different from that of another vital sign feature (HR, Conv_HF, PSV, etc. . . . ).

In the same example of FIG. 7, after calculating the indication values 702a-702c for the intermediate epoch, the processor 101 performs a further logistic regression operation 702' to determine the sleep stage of the intermediate epoch based on the corresponding indication values 702a-702c. The further logistic regression operation 702' uses a model independent of or separate from those of the logistic regression operations 701a'-701c'. Specifically, the processor 101 performs on the indication values 702a-702c of the respective intermediate epoch the further logistic regression operation to calculate an REM value 703 for the respective intermediate epoch. For the respective intermediate epoch, the processor 101 determines that the epoch corresponds to REM if the REM value exceeds a predetermined threshold (e.g., 0.5) and to NREM if otherwise. In the event of missing data as discussed in relation to FIG. 6, an epoch is determined to correspond to an unknown sleep stage. Each logistic regression operation 701a'-701c' (marked in FIG. 7 by the indication "Regression") may be considered to be a first-stage logistic operation whilst the further logistic operation 702' (marked in FIG. 7 by the indication "Further regression") may be considered to be a second-stage logistic operation.

It can be appreciated that each logistic regression operation 701a'-701c' relies on feature values of the respective vital sign feature extracted from the input physiological signal (e.g., a PPG signal) to calculate the respective indication value 702a-702c for each epoch. The further logistic regression operation 702' then takes the resultant indication values 702a-702c of each epoch as inputs to calculate an REM value 703 for the epoch. In this embodiment, the further logistic regression operation 702' uses the same sigmoid operation as the operations 701a'-701c' but with different weights.

It is worth noting that the further logistic regression operation 702' can be performed with at least two of the indications values 702a-702c. That is to say, where one of the indication values 702a-702c of a particular epoch is non-descriptive or inconclusive (e.g., having a value of zero) due to, for example, unsuccessful compensation or non-compensation, the further logistic regression operation 702' is performed based on the other two of the indication values 702a-702c of the particular epoch. That is to say, the further logistic regression operation 702' is performed further based on said one of the indication values 702a-702c if said one of the indication values 702a-702c is descriptive of the sleep stage of the particular epoch. In other words, the further logistic regression operation 702' requires at least two indication values that are descriptive of the corresponding epoch, allowing any additional, non-descriptive indication values to be omitted from the further logistic regression operation 702'. This prevents or reduces accuracy of sleep stage detection from being adversely affected by indication values that are non-descriptive of the sleep stage, which may be caused by unsuccessful sensor detection. To facilitate this, the logistic regression operations 701a'-701c' may use models independent of or separate from one another.

Figure 8:
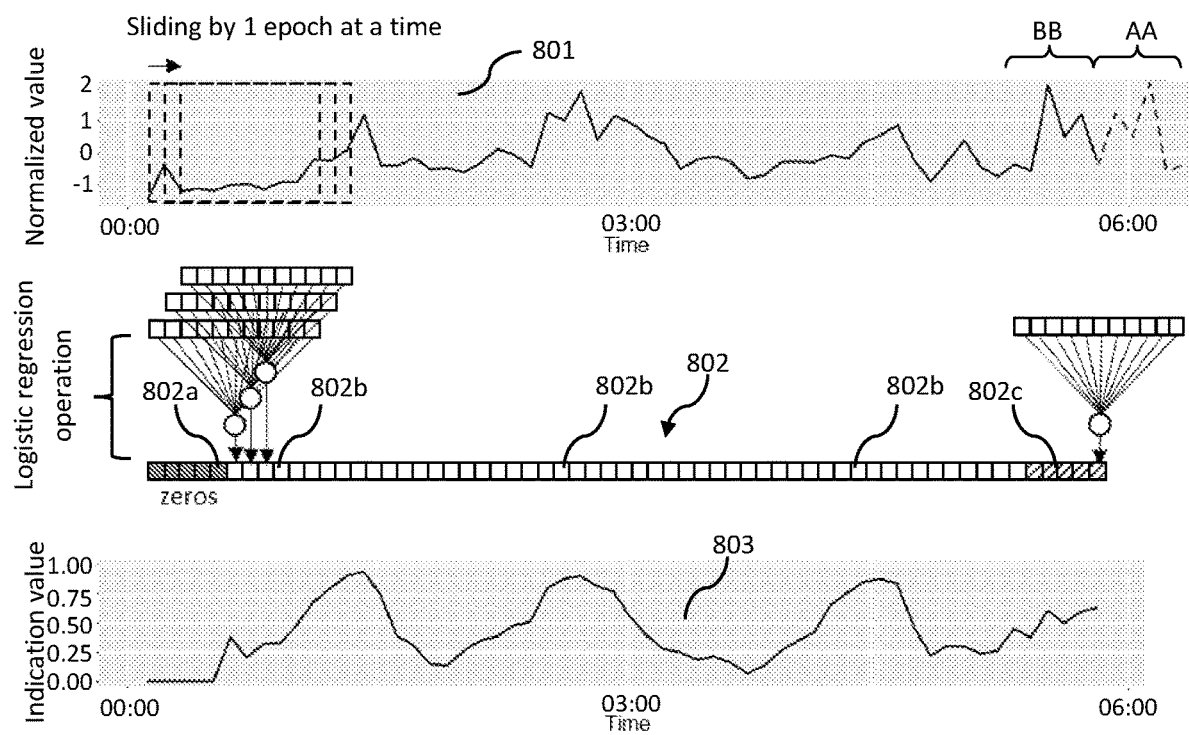
FIG. 8 shows an example scenario of the computing device of FIG. 1 performing a logistic regression operation in a manner of sliding window.

The process of FIG. 7 is performed, in this embodiment, sequentially for each intermediate epoch in the manner of a sliding window (11 epochs) of logistic regression. With reference to FIG. 8, the processor 101 performs the logistic regression operation 701a'-701c' with respect to each vital sign feature 701a-701c to calculate an indication value 702a-702c for each intermediate epoch of the vital sign feature 701a-701c. Normalised feature values of one of the vital sign features 701a-701c are shown in a line chart 801. Among all epochs represented by a series of blocks 802, the intermediate epochs for sleep stage calculation are represented by respective ones of unshaded blocks 802b and diagonally shaded blocks 802c. The normalised feature values of the line chart 801 range from −1 to 2 in this embodiment, and may have a different range in other embodiments. The first five epochs (considered non-intermediate) represented by shaded blocks 802a are each predetermined to have a feature value of zero and are identified as NREM. This is consistent with the fact that a sleep session begins with a NREM period, which typically ranges from 30 minutes to 70 minutes. In the sliding window manner, the processor 101 sequentially calculates an indication value 702a-702c for each subsequent, intermediate epoch towards the end of the sleep session (marked by the last one of the diagonally shaded blocks 802c), in the manner described above. The calculated indication values 702a-702c are shown in a line chart 803.

To perform the calculation for the last five epochs (marked by the diagonally shaded blocks 802c) which have fewer than five succeeding epochs, the vital sign feature 701a-701c is extended by five extension epochs (not shown) with feature values mirroring those of the last five epochs. The dashed line portion (marked by "AA" in FIG. 8) at the end of the line chart 801 corresponds to the extension epochs and mirrors the solid line portion (marked by "BB" in FIG. 8) corresponding to the last five epochs preceding the extension epochs. The dashed line portion ("AA") may otherwise be considered to be a flipped or mirrored extension of the solid line portion ("BB") of the last five epochs concatenated to the same. Thus, the last five epochs at the end of the sleep session (i.e., the diagonally shaded blocks 802c) also serve as intermediate epochs for the purpose of the calculation. In the manner described hereinabove, the indication values 702a-702c are calculated for respective intermediate epochs of the vital sign feature 701a-701c. In other embodiments, the calculation of the indication value 702a-702c for each intermediate epoch may take into account any equal or unequal numbers of preceding and succeeding epochs. For example, the numbers of preceding and succeeding epochs may be two, whereby, for the calculation of the indication value of each intermediate epoch, five epochs are used.

Figure 9:
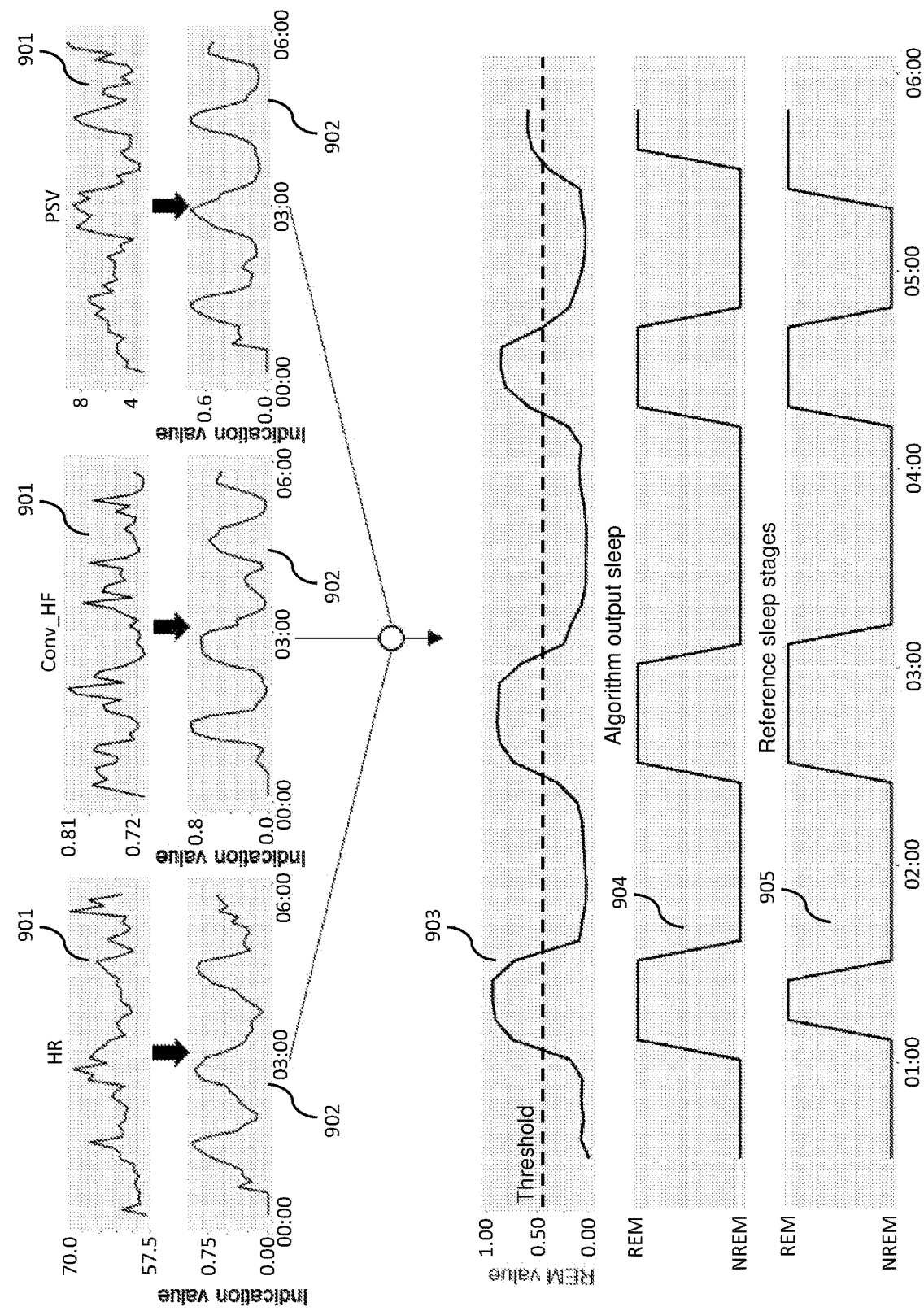
FIG. 9 shows line charts of different signals at different stages of calculation performed by the computing device of FIG. 1.

FIG. 9 is a diagram showing line charts 901 of three vital sign features (HR, Conv_HF and PSV), line charts 902 of indication values calculated from the vital sign features using the logistic regression operations, a line chart 903 of REM values calculated from the indication values using the further logistic regression operation, a line chart 904 of sleep stage information derived from the line chart 903 based on a threshold value, and a line chart 905 of reference sleep information for comparison with the line chart 904. For each epoch, the epoch is determined to correspond to REM if the corresponding REM value exceeds the threshold value (e.g., 0.5), and to correspond to NREM if otherwise. The threshold value may be other than 0.5, depending on implementation.

Figure 10:
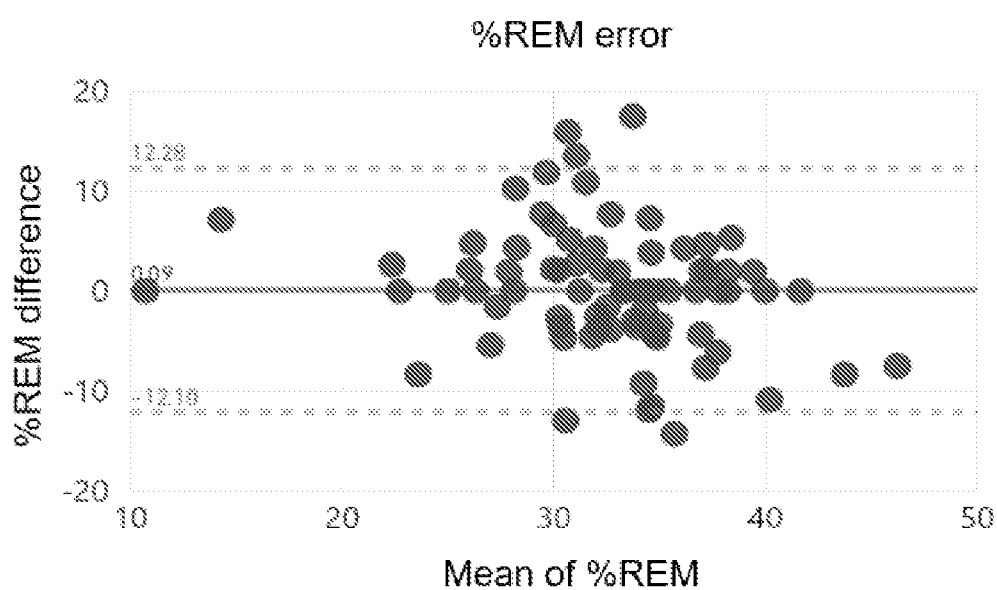
FIG. 10 shows a Bland-Altman plot of error percentage for a result of sleep stage detection obtained using the method of FIG. 2.

FIG. 10 is a Bland-Altman plot showing an error percentage of REM values calculated according to the embodiment of FIG. 1 with reference to reference sleep stage information over 50 nights. The x-axis shows mean values of error percentage while the y-axis shows values representing differences of error percentage. The horizontal line shows a mean difference value of 0.09%, while the dashed lines above and below the horizontal line show confident intervals of error of −12.10 and 12.28, respectively. The closer the horizontal line to zero and the closer the dots are from the horizontal line, the more accurate the calculated REM values.

Figure 11:
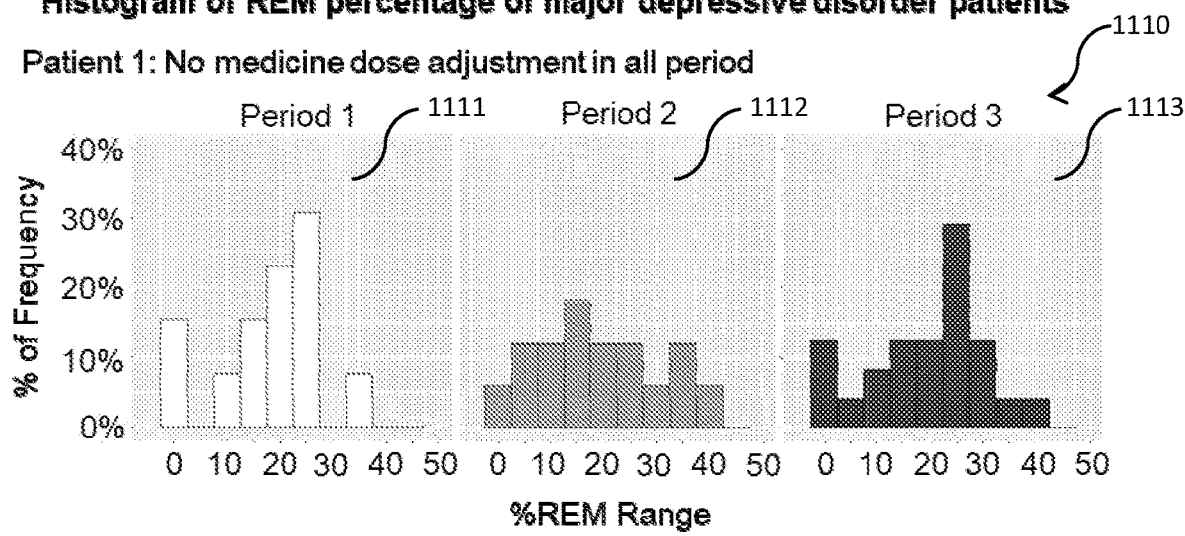
FIG. 11 shows histograms of REM percentage and frequency for major depressive disorder patients.
Figure 11:
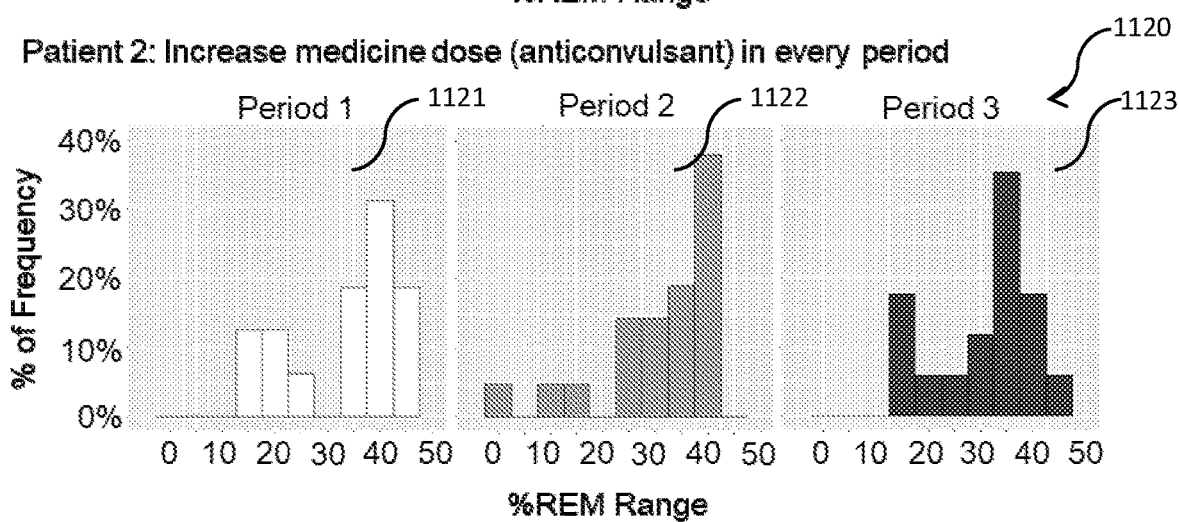

FIG. 11 shows first and second rows 1110, 1120, each of which includes three histograms of REM percentage determined in the manner described above for a respective test subject. The test subject in this example is a depressive disorder patient, and in other applications may be a healthy person wishing to make adjustments to his or her sleep pattern. Each row 1110, 1120 includes a first histogram 1111, 1121 corresponding to a first period (labelled as "Period 1"), a second histogram 1112, 1122 corresponding to a second period (labelled as "Period 2") after the first period, and a third histogram 1113, 1123 corresponding to a third period (labelled as "Period 3") after the second period. The test subject of the first row 1110 receives the same, unadjusted dosage of anticonvulsant before the first period, between the first and second periods, and between the second and third periods. The test subject of the second row 1120 receives an initial dosage of anticonvulsant before the first period, an increased dosage of anticonvulsant between the first and second periods, and a further increased dosage of anticonvulsant between the second and third periods. It can be observed that the patient of the second row 1120 continues to experience high frequency of occurrence of sleep with high REM percentage range. Each of the first, second and third periods represents a full cycle of sleep (i.e., a full sleep session) in this scenario. In other applications, each period may represent more cycles of sleep. Different test subjects may have full cycles of sleep of different lengths.

The information represented by the histograms 1111-1113, 1121-1123 may serve as a basis for determining a prescriptive medical dose or dosage to be administered to the test subjects for adjusting REM range and frequency experienced by the test subjects. The prescriptive medical dose or dosage may relate to anticonvulsant, benzodiazepines, emazepam, or any receptor agonists capable of alleviating insomnia.

Specifically, a method of assessing a responsiveness to a medical dosage according to one embodiment includes: receiving sleep stage information of a first time period; receiving sleep stage information of a second time period for comparison with that of the first time period; and assessing a responsiveness to a medical dosage occurring between the first and second time periods based on a result of the comparison. In the example of the test subject of the first row 1110, between the second and third periods, an assessment of responsiveness of the test subject to the unadjusted medical dosage occurring between the first and second periods can be made by receiving and comparing the sleep stage information of the first and second periods. In the example of the test subject of the second row 1120, between the second and third periods, an assessment of responsiveness of the test subject to the increased medical dosage occurring between the first and second periods can be made by receiving and comparing the sleep stage information of the first and second periods. A result of the assessment may serve as basis for maintaining or adjusting a further medical dosage to occur between the second and third periods, with the responsiveness of the test subject to the further medical dosage to be assessed after the third period. It can be then appreciated that a method of deriving a medical dosage according to one embodiment includes: receiving sleep stage information of a first time period; receiving sleep stage information of a second time period for comparison with that of the first time period; and providing a medical dosage based on a result of the comparison.

Figure 12A:
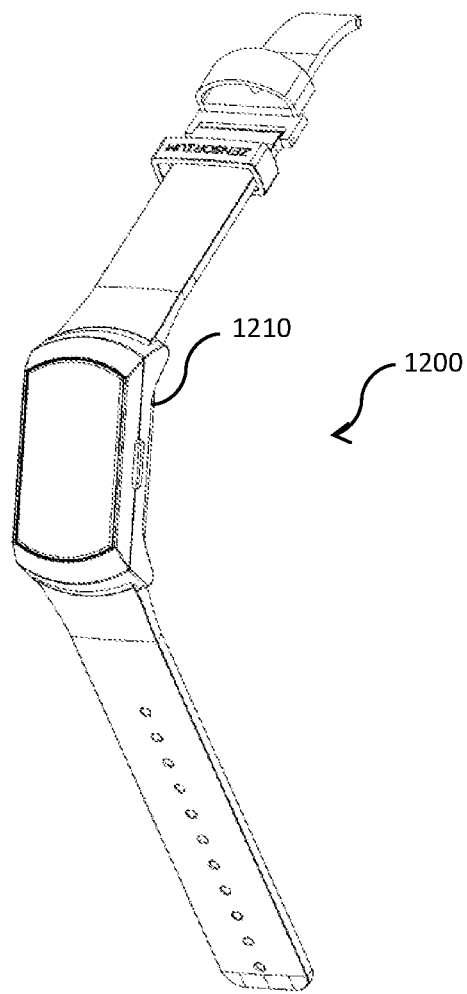
FIG. 12A shows an embodiment of the computing device of FIG. 1 in the form of a wristwatch or wearable device.
Figure 12B:
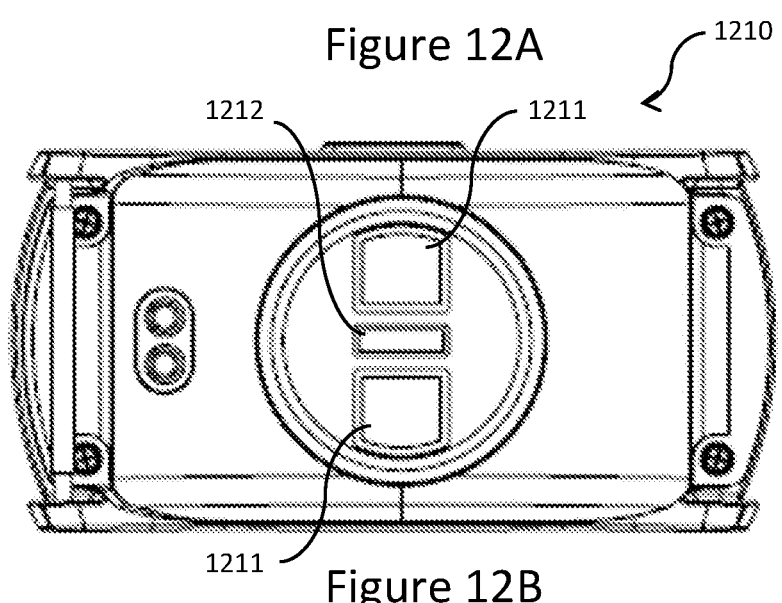
FIG. 12B shows a schematic representation of a head assembly of the wearable device of FIG. 12A.
Figure 12C:
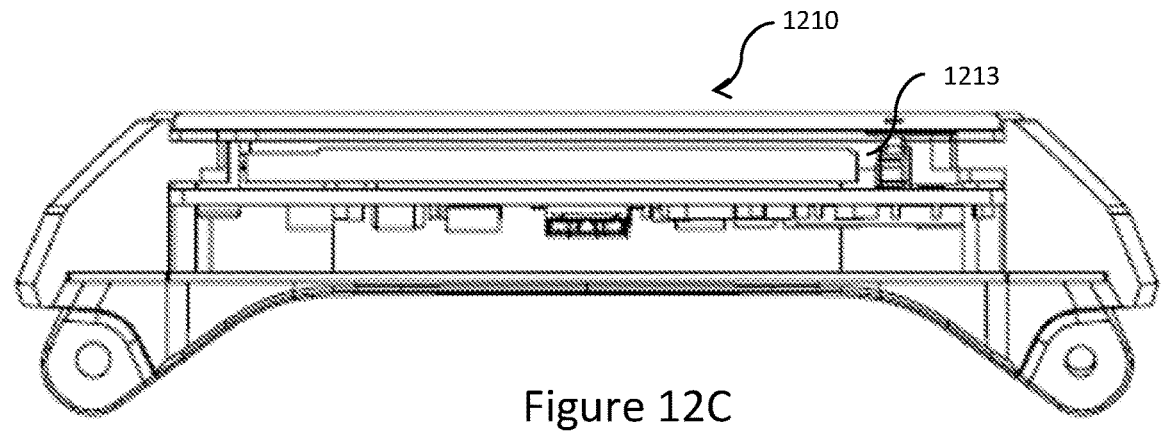
FIG. 12C shows a cross-sectional schematic view of the head assembly of FIG. 12A.
Figure 13:
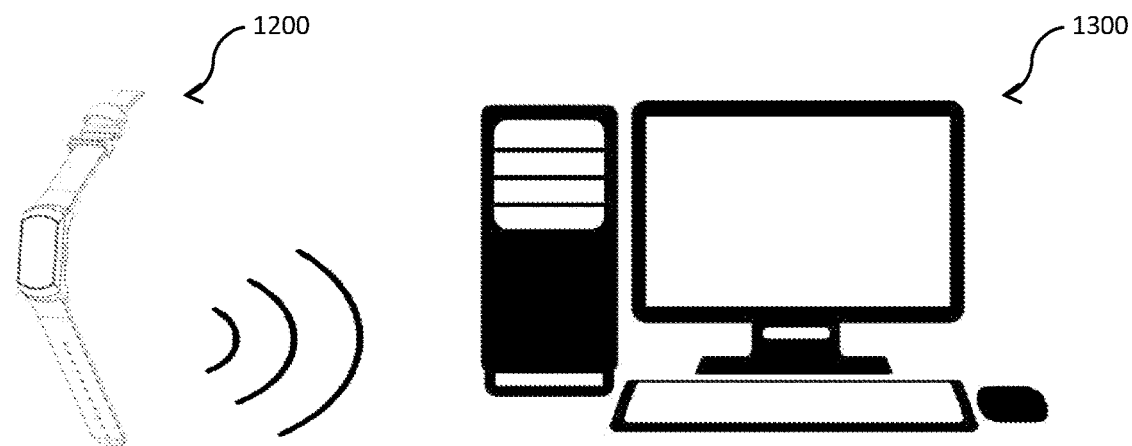
FIG. 13 shows an instance of wireless transmission of calculated sleep stage information from the wearable device of FIG. 12A to another computing device in an example scenario.

FIG. 12A shows an embodiment of the computing device 100 of FIG. 1 in the form of a wristwatch or wearable device 1200. Further referring to FIGS. 12B and 12C, the wearable device 1200 includes a head assembly 1210, which includes, among other components, two physiological sensors 1211 (one of which is the physiological sensor 104 of FIG. 1), an illumination element 1212 and a wireless communication module 1213. The physiological sensors 1211 and the illumination element 1212 together form the physiological sensor 104 operatively associate with the processor 101. The wireless communication module 1213 serves to provide the wireless function of the communication interface 105 associated with the processor 101. The firmware chip 102 and/or the storage device 103 may store the instructions for the processor 101 to perform any of the steps of the methods of 200-500. For example, for the purpose of step 201, the physiological sensors 1211 and the illumination element 1212 are controlled by the processor 101 to capture physiological signals of a user wearing the wearable device 1200. Further, where the wearable device 1200 performs step 205, the calculated sleep stage of each epoch may be wirelessly provided by the processor 101 via the wireless communication module 1213. The calculated sleep stage thus transmitted may constitute sleep stage information. Further referring to FIG. 13, another computing device 1300 (e.g., a personal computer or a server device with components similar to those shown in FIG. 1) may wirelessly receive, from the wearable device 1200, such sleep stage information of first and second time periods and compare the received sleep stage information. The computing device 1300 may then provide a medical dosage based on a result of the comparison, or may assess a responsiveness to a medical dosage occurring between the first and second time periods based on a result of the comparison.

In an alternative embodiment involving a single vital sign feature (e.g., the first vital sign feature 701a), since the first indication value 702a of an intermediate epoch resulting from the corresponding first logistic regression operation 701a' is descriptive of the sleep stage of the intermediate epoch, the further logistic regression operation 702' can be omitted and the first indication value 702a may serve as the REM value 703 for sleep stage determination.

The invention claimed is:

1. A method of sleep stage detection, the method comprising:
receiving a first vital sign feature derived from a photoplethysmography (PPG) signal, the first vital sign feature including a plurality of first feature values corresponding to respective ones of a plurality of epochs;
performing a first logistic regression operation to calculate a first indication value for each intermediate one of the epochs based on the corresponding first feature value and those of preceding and succeeding ones of the epochs that precede and succeed, respectively, the corresponding intermediate epoch, the first indication value being descriptive of a sleep stage of the corresponding intermediate epoch; and
detecting the sleep stage of the corresponding intermediate epoch based on the first indication value for the corresponding intermediate epoch,
wherein the first logistic regression operation is performed using a machine learning classifier model.

2. The method of claim 1, wherein the first vital sign feature relates to one of a heart rate, a pulse shape variability and a convoluted high frequency power of heart rate variability.

3. The method of claim 1, wherein the first logistic regression operation includes weighting and sigmoid operations.

4. The method of claim 1, further comprising:
receiving a second vital sign feature derived from the PPG signal, the second vital sign feature including a plurality of second feature values corresponding to respective ones of the epochs, the second vital sign feature belonging to a user of the first vital sign feature;
performing a second logistic regression operation to calculate a second indication value for each intermediate one of the epochs based on the corresponding second feature value and those of the preceding and succeeding ones of the epochs that precede and succeed, respectively, the corresponding intermediate epoch, the second indication value being descriptive of the sleep stage of the corresponding intermediate epoch;
performing a further logistic regression operation to determine the sleep stage of each intermediate one of the epochs based on the corresponding first and second indication values; and
detecting the sleep stage of each intermediate epoch based on the first and second indication values for the intermediate epoch.

5. The method of claim 4, wherein one of the logistic regression operations have weight values different from those of another one of the logistic regression operations.

6. The method of claim 4, further comprising:
receiving a third vital sign feature derived from the PPG signal, the third vital sign feature including a plurality of third feature values corresponding to respective ones of the epochs, the third vital sign feature belonging to the user of the first vital sign feature; and
performing a third logistic regression operation to calculate a third indication value for each intermediate one of the epochs based on the corresponding third feature value and those of the preceding and succeeding ones of the epochs that precede and succeed, respectively, the corresponding intermediate epoch,
performing the further logistic regression operation to determine the sleep stage of each intermediate one of the epochs further based on the corresponding third indication value if the corresponding third indication value is descriptive of the sleep stage of the corresponding intermediate epoch; and
detecting the sleep stage of each intermediate epoch further based on the third indication value for the intermediate epoch if the third indication value is descriptive of the sleep stage of the corresponding intermediate epoch.

7. The method of claim 1, further comprising training the machine learning classifier model for logistic regression operation, said training comprising:
receiving a training vital sign feature in association with reference sleep stage information;
generating, from the training vital sign feature and the reference sleep stage information, a cross validation set including a plurality of subsamples;
calculate each one of the subsamples with reference to other ones of the subsamples using the machine learning classifier model with each of a plurality of machine learning parameter sets; and
associating the machine learning classifier model with one of the parameter sets based on a comparison of the reference sleep stage information with a result of the calculation.

8. The method of claim 7, wherein the training vital sign feature relates to one of a heart rate, a pulse shape variability and a convoluted high frequency power of heart rate variability.

9. The method of claim 7, further comprising:
receiving a further training vital sign feature in association with the reference sleep stage information, the further training vital sign feature belonging to a user of the training vital sign feature and being different from the training vital sign feature,
wherein the cross validation set is further generated from the further training vital sign feature.

10. The method of claim 7, wherein generating the cross validation set comprises:
combining the training vital sign feature with the reference sleep stage information to derive the cross validation set.

11. The method of claim 7, wherein the training vital sign feature is sliced by at least three consecutive epochs.

12. The method of claim 11, wherein the at least three consecutive epochs include, with respect to an intermediate one of the epochs, a preceding one, the intermediate one and a succeeding one of the epochs.

13. The method of claim 11, wherein the at least three consecutive epochs include 11 epochs.

14. The method of claim 11, wherein the at least three consecutive epochs are configured to correspond to a total window period of at least 30 minutes.

15. The method of claim 7, wherein the training vital sign feature is normalised.

16. The method of claim 7, wherein the training vital sign feature is compensated for a missing portion.

17. The method of claim 16, wherein the missing portion is compensated for using max pooling.

* * * * *